(12) United States Patent
Leconte

(10) Patent No.: US 9,079,823 B2
(45) Date of Patent: Jul. 14, 2015

(54) PREPARATION OF DIAMINE VIA THE PREPARATION OF AMINONITRILE

(75) Inventor: Philippe Leconte, Ribeauville (FR)

(73) Assignee: RHODIA OPERATIONS, Aubervilliers (FR)

(*) Notice: Subject to any disclaimer, the term of this patent is extended or adjusted under 35 U.S.C. 154(b) by 0 days.

(21) Appl. No.: 13/982,694

(22) PCT Filed: Feb. 3, 2012

(86) PCT No.: PCT/EP2012/051882
§ 371 (c)(1),
(2), (4) Date: Aug. 1, 2013

(87) PCT Pub. No.: WO2012/104420
PCT Pub. Date: Aug. 9, 2012

(65) Prior Publication Data
US 2014/0012045 A1 Jan. 9, 2014

(30) Foreign Application Priority Data

Feb. 4, 2011 (FR) ...................................... 11 50908

(51) Int. Cl.
*C07C 209/48* (2006.01)
*C07C 253/30* (2006.01)

(52) U.S. Cl.
CPC .............. *C07C 209/48* (2013.01); *C07C 253/30* (2013.01)

(58) Field of Classification Search
None
See application file for complete search history.

(56) References Cited

U.S. PATENT DOCUMENTS

| 4,172,091 | A | 10/1979 | Weber et al. |
| 6,478,968 | B1 | 11/2002 | Perrona et al. |
| 6,518,449 | B1 | 2/2003 | Boschat et al. |
| 6,951,959 | B2 | 10/2005 | Ward et al. |
| 7,723,547 | B2 * | 5/2010 | Ernst et al. ..................... 564/490 |
| 2007/0118001 | A1 | 5/2007 | Bocquenet et al. |
| 2008/0293973 | A1 | 11/2008 | Ernst et al. |
| 2009/0069590 | A1 * | 3/2009 | Eberhardt et al. ............ 558/452 |
| 2010/0105952 | A1 * | 4/2010 | Ernst et al. ..................... 564/490 |
| 2010/0267989 | A1 | 10/2010 | Letourneur et al. |
| 2012/0029225 | A1 * | 2/2012 | Magerlein et al. ............ 558/452 |
| 2012/0071694 | A1 * | 3/2012 | Eberhardt et al. ............ 564/490 |

FOREIGN PATENT DOCUMENTS

| DE | 58 306 | 10/1967 |
| DE | 222 011 | 5/1985 |
| FR | 2 749 191 A1 | 12/1997 |
| FR | 2 773 086 A1 | 7/1999 |
| FR | 2 834 984 A1 | 7/2003 |
| FR | 2 921 922 A1 | 4/2009 |
| RO | 69448 | 8/1989 |
| WO | 2009/043906 A1 | 4/2009 |

OTHER PUBLICATIONS

International Search Report issued on Mar. 21, 2012, by the European Patent Office as the International Searching Authority in International Patent Application No. PCT/EP2012/051882.

* cited by examiner

*Primary Examiner* — Brian J Davis
(74) *Attorney, Agent, or Firm* — Xuping Fu

(57) ABSTRACT

A continuous method (P) for preparing diamine is described. The method includes reacting the corresponding alkene nitrile with the corresponding monoamine in order to form the corresponding aminonitrile. The monoamine can be introduced in molecular excess with respect to the alkene nitrile, wherein the unreacted monoamine is recirculated to the reaction; followed by reducing the aminonitrile produced by hydrogen in the presence of at least one alkali-metal hydroxide, water, and a hydrogenation catalyst; and purifying the diamine.

14 Claims, No Drawings

PREPARATION OF DIAMINE VIA THE PREPARATION OF AMINONITRILE

CROSS-REFERENCE TO PRIOR APPLICATIONS

This application is a National Stage of PCT/EP2012/051882, filed Feb. 3, 2012, and designating the United States (published in French on Aug. 9, 2012, as WO 2012/104420 A1), which claims priority under 35 U.S.C. §119 to FR 1150908, filed Feb. 4, 2011, each hereby expressly incorporated by reference in its entirety and each assigned to the assignee hereof.

The present invention relates to a continuous process for preparing diamine via the preparation of aminonitrile by reaction between the corresponding monoamine and the corresponding alkenenitrile.

The present invention more particularly relates to a continuous process for preparing dimethylaminopropylamine (N,N-dimethyl-1,3-propanediamine or DMAPA) via the preparation of 3-(dimethylamino)propanenitrile (DMAPN) by reaction of dimethylamine (DMA) with acrylonitrile (AN).

DMAPA has many uses, especially in the field of hardeners, bonding agents, ion exchangers, flocculation aids, pigments or pesticides. The amounts of DMAPA produced are thus on the increase. It is important, for some of these applications, to provide a process for preparing pure DMAPA, continuously and at reduced cost.

Processes are known, especially from US 2008/0293973, for preparing DMAPA in three steps: a first step of reaction between DMA and AN to form dimethylaminopropionitrile (DMAPN); a second step of hydrogenating the DMAPN to form DMAPA; and finally a step of purifying the DMAPA obtained. Usually, DMA and AN are introduced into the reactor in stoichiometric amount or with an excess of DMA.

However, the drawback of the stoichiometric introduction is that the yield is insufficient. DMA has a very low boiling point (of about 7° C.) and thus, when it is introduced in excess, if it is desired to recycle the unreacted DMA, a distillation must be performed, and also condensation of the DMA vapors obtained, which places a substantial burden on the production installations and increases the manufacturing cost.

It is moreover already known practice to hydrogenate the aminonitrile (DMAPN) obtained in the presence of an alkali metal hydroxide and a catalyst (U.S. Pat. No. 6,951,959).

It is thus necessary to provide a process for preparing diamine and especially DMAPA, which provides a solution to all or some of the problems of the prior art processes.

A first object of the present invention is to provide a process for continuously preparing diamine, especially DMAPA, and for recycling the reagents introduced in excess.

An object of the invention is also to provide a process that is industrially advantageous.

Another object of the present invention is to provide a process for purifying the diamine obtained, especially DMAPA, which makes it possible to obtain a purity of greater than 99.5%, and which is easy to perform.

Yet another object of the present invention is to provide a process which makes it possible:
- to limit the formation of byproducts and especially of byproducts that are difficult or even impossible to separate out via the usual techniques;
- to control the heat of reaction;
- to avoid the degradation of the products formed;
- to facilitate the recycling of the monoamine introduced in excess; and/or
- to increase the selectivity and the yield of diamine, especially of DMAPA.

Other objects will become apparent on reading the description of the invention.

The present invention relates to a continuous process (P) for preparing diamine, comprising the steps of:
(a) reaction between the corresponding alkenenitrile and the corresponding monoamine to form the corresponding aminonitrile, the monoamine being introduced in molar excess relative to the alkenenitrile, with recycling into the reaction of the unreacted monoamine;
(b) reduction of the aminonitrile obtained in step (a) with hydrogen in the presence of at least one alkali metal hydroxide, water and a hydrogenation catalyst;
(c) separation of the alkali metal hydroxide by evaporation of the diamine obtained in step (b) and of the water;
(d) distillation of the diamine.

For the present invention, "the corresponding alkenenitrile" and the "corresponding monoamine" are compounds for obtaining the diamine of desired structure by means of the process of the invention, in particular by performing a Michael addition followed by hydrogenation.

The alkenenitrile comprises at least one carbon-carbon double bond. It is preferably chosen from linear or branched $C_1$ to $C_4$ alkenes, in which a hydrogen atom is replaced with a conjugated cyano group, i.e. the alkenenitrile comprises a double bond in the $\alpha,\beta$ position relative to the cyano group. By definition, the linear or branched alkenes corresponding to the definition of the invention are $C_2$ to $C_4$. Examples of $C_2$ to $C_4$ alkenes are especially ethene, propene, 1-butene, 2-butene and 2-methylpropene. Examples of nitriles are acrylonitrile, 2-butenenitrile, methacrylonitrile, 2-pentenenitrile, 2-ethylacrylonitrile, 2-methyl-2-butenenitrile and 3-methyl-2-butenenitrile.

Preferably, the alkenenitrile is acrylonitrile (AN).

The monoamine is preferably a secondary amine of general formula $R^1R^2NH$, in which $R^1$ and $R^2$, which may be identical or different, represent a $C_1$ to $C_4$ alkyl. Examples of $C_1$ to $C_4$ alkyls that may be mentioned include methyl, ethyl, n-propyl, i-propyl, 1-n-butyl, 2-n-butyl, i-butyl and t-butyl.

Preferably, the monoamine is dimethylamine (DMA).

Preferably, the intermediate aminonitrile is 3-(dimethylamino)propanenitrile (DMAPN) resulting from the addition of dimethylamine (DMA) to acrylonitrile (AN).

In a particularly preferred manner, the process of the invention relates to the preparation of DMAPA by hydrogenation of DMAPN.

During step (a) of the process of the invention, the monoamine is introduced in excess, especially an excess of at least 0.1 mol % relative to the alkenenitrile, preferably between 1 mol % and 50 mol % and more preferably between 5 mol % and 25 mol %.

In a particularly advantageous manner, step (a) is performed in one or more reactors in series of piston type with recycling of the excess monoamine and of some of the aminonitrile.

It is possible to use two piston reactors in series. In this case, and advantageously, the volume of the second reactor may be up to 2, 3, 4, 5, 10, 25 or 50 times greater than the volume of the first reactor.

The monoamine, especially dimethylamine (DMA), has a very low boiling point (about 7° C. for DMA) and recycling of the excess monoamine is generally performed by distillation followed by condensation of the monoamine vapors. Usually, this condensation requires a refrigeration unit or a compressor, which induces a substantial cost.

The process of the present invention makes it possible to overcome this problem by dissolving in a fraction of the aminonitrile obtained in step (a) the excess, recycled monoamine leaving the separation system as described hereinbelow, in gaseous form.

The recycling of the monoamine may be performed using an absorption system in which the gaseous monoamine is dissolved in a fraction of the aminonitrile obtained in step (a). The monoamine may be conveyed to the absorption system via a vacuum device such as a vacuum pump, for example an ejector, a liquid ring pump, a roots or dry pump, or an assembly of these devices. As examples of assemblies of vacuum devices, mention may be made, without being limited thereto, of the dry pump and then ejector assembly or the roots pump and then liquid ring pump assembly.

In a particularly advantageous manner, the vacuum device also makes it possible to reduce the pressure in the distillation column and to lower the boiling point of the aminonitrile obtained, thus limiting its degradation and consequently the formation of unwanted byproducts.

Examples of absorption systems that may be mentioned include absorption columns and reactors.

Advantageously, the pressure in the vacuum device is between 0.01 and 0.08 MPa.

The recycling of step (a) uses a separation system, for example a flash column and/or a distillation column, which makes it possible to recover:
  on the one hand, the aminonitrile, a first fraction of which is sent to a reactor for step (b) and a second fraction of which is sent to an absorption system to enable dissolution of the excess monoamine; and
  on the other hand, the excess monoamine in gaseous form, which is sent, for example by means of a vacuum device, to the absorption system which enables its dissolution in the second fraction of aminonitrile, the whole then especially being recycled into the reaction of step (a).

Thus, and advantageously, a fraction of the aminonitrile obtained in step (a) also serves as solvent for this step.

In general, the monoamine and the alkenenitrile may be introduced directly into the reactor, part of the monoamine introduced consisting of recycled monoamine dissolved in the aminonitrile. The introduction of reagents into the reactor may be performed by means of a static mixer.

Preferably, the temperature during step (a) is between 25 and 110° C. When several reactors are used in step (a), the temperature in each reactor is independently between 25 and 110° C.

Advantageously, step (b) is performed in a reactor comprising means for separating out the catalyst, such as a decanter and/or a tangential filtration system.

The reactor may be a piston-type reactor or a stirred reactor, and is preferably a piston-type reactor.

The apparatus that is suitable for performing step (b) of the process of the invention makes it possible to achieve excellent gas/liquid contact, rapid and efficient separation of these two phases after contact, continuous separation of the hydrogenate and of the catalyst, and also recycling of the latter, in a time that is compatible with the least possible deactivation of the catalyst.

The reactor of step (b) is especially a piston reactor which may comprise three main sections: a piston reaction section functioning according to the bubble column principle with circulation of a bed of catalyst in suspension, a gas/liquid separation section and a catalyst/liquid separation section with recycling of the catalyst and withdrawal of the liquid (hydrogenate). The apparatus also has, at the piston reactor outlet, a zone for decantation of the catalyst particles, the supernatant phase being recycled into the piston reactor via a first external loop comprising sampling of the medium containing the diamine, the decanted phase being recycled into the piston reactor via a second external loop.

Such apparatus is especially described in patent application WO 2009/043906 (especially p. 10, l. 6 to p. 12, l. 27).

Another apparatus that may be used in the process of the invention is apparatus using tangential filtration. The use of such apparatus consists in continuously and tangentially filtering through a membrane filter at least part of a three-phase reaction mixture comprising a liquid phase in which is especially found the diamine formed, a gaseous phase comprising hydrogen and a catalytic solid phase. This apparatus enables the catalyst to be recycled while at the same time recovering at least part of the filtrate containing the reaction products. Such tangential filtration apparatus is especially described in FR 2749191. The use of such apparatus is described in FR 2834984.

The catalysts that are suitable for use in step (b) are Raney metals such as Raney nickel or Raney cobalt. Preferably, the catalyst is Raney nickel, for example doped Raney nickel.

Promoter elements, or dopants, may advantageously be incorporated into the Raney metal; they are then chosen from the elements belonging to groups IIB, IVB, VIA, VIIB and VIII of the Periodic Table of the Elements. Preferably, the promoters are chosen from titanium, chromium, zirconium, vanadium, molybdenum, manganese, cobalt, nickel, zinc and iron, and combinations thereof in all proportions.

The weight amount of dopant element in the catalyst is generally less than 10% and preferably less than 5%.

Advantageously, the catalyst may be separated out, and all or some of this catalyst may then be subjected to a regeneration step before being recycled into step (b).

Various regeneration processes may be performed.

A first regeneration process comprises:
 (i) a step of washing the catalyst with water (especially so as to remove the majority of the organic compounds);
 (ii) a step of treatment with a base; and
 (iii) a step of washing with an aqueous alkali metal hydroxide solution or water.

Step (i) is advantageously repeated to obtain in the final washing water a concentration of organic compounds of less than or equal to 1% by weight. This concentration may especially be determined by the amount of diamine contained in the washing water. This step may also be performed continuously in one or more counter-current-flow columns or in a column comprising the catalyst to be regenerated in the form of a fixed bed. Advantageously, the temperature during this step (i) is between 10 and 50° C. and preferably between 20 and 35° C. (room temperature).

The bases that are suitable for use in step (ii) are especially alkali metal hydroxides, preferably sodium hydroxide. The base solution used preferably contains from 10% to 25% by weight of alkali metal hydroxide. This step is advantageously performed at a temperature above 80° C. and preferably above the boiling point of the base.

The duration of this step (ii) should be sufficient to enable regeneration of the catalytic activity corresponding to at least 60% of the catalytic activity of the fresh catalyst, advantageously at least 65%. This treatment advantageously makes it possible to produce hydrogen, which will condition the catalyst for its subsequent use.

The washing of step (iii) may be repeated, and is advantageously performed with water at a temperature of between 40 and 90° C. It is also possible to use, as washing liquid, an aqueous solution of an alkali metal hydroxide, preferably sodium hydroxide, at a minimum concentration of 0.012 g/l of alkali metal hydroxide and advantageously between 0.012% by weight and 0.040% by weight of alkali metal hydroxide. The washing is advantageously performed until a weight concentration of alkali metal hydroxide (sodium hydroxide) of greater than or equal to 0.012% is obtained in the final washing water.

This first regeneration process may be performed under an inert atmosphere or an atmosphere not comprising oxygen. This process is especially as described in FR 2921922.

A second regeneration process consists of a treatment with hydrogen comprising
 (i) a step of washing the catalyst with water (especially so as to remove the majority of the organic compounds);
 (ii) a step of treatment under a pressure of hydrogen in a sodium hydroxide solution at a temperature below 130° C.;
 (iii) washing of the catalyst with water or a basic aqueous solution, especially to a final pH of the washing waters of between 12 and 13.

Such a process is especially described in FR 2773086.

Finally, it is possible to regenerate the catalyst by treatment with water. Such a regeneration process is especially the process described in U.S. Pat. No. 6,951,959 (column 5, lines 45-58) or in U.S. Pat. No. 4,429,159.

These various regeneration processes make it possible to obtain a regenerated catalyst having catalytic activity corresponding to 35% to 100% and preferably 40% to 90% of the catalytic activity of the fresh catalyst.

The term "fresh catalyst" means a catalyst that has not been used in the hydrogenation reaction of the process of the invention.

The definition and calculation of the activity of a catalyst are as described on pages 5 to 7 of international patent application WO 2009/043906.

After washing, the regenerated catalyst is recycled into the reaction of step (b) or mixed with fresh catalyst before being recycled into the reaction of step (b), especially before introduction into the reactor of step (b).

Thus, according to one embodiment, it is possible to use a mixture of fresh catalyst and of regenerated catalyst.

The mass ratio of fresh catalyst relative to the regenerated catalyst is between 1/99 and 80/20.

According to another embodiment, step (b) uses only fresh catalyst.

Step (b) may be performed in the presence of a solvent, which may advantageously be the product of the hydrogenation.

The amount of water used during step (b) is less than or equal to 50% and advantageously less than or equal to 20% by weight of the liquid phase of the total reaction flow of step (b), for example between 0.1% and 15% by weight.

Preferably, in step (b), the alkali metal hydroxide is chosen from LiOH, NaOH, KOH, RbOH and CsOH, and mixtures thereof. NaOH and/or KOH are particularly preferred.

In a particular embodiment, only one alkali metal hydroxide is used during step (b).

The amount of alkali metal hydroxide used is at least 0.1 mol of alkali metal hydroxide per kg of catalyst, preferably between 0.1 and 2 mol, for example between 0.3 and 1.5 mol.

Advantageously, step (b) may be performed at a temperature of less than or equal to 150° C., preferably less than or equal to 120° C. and even more preferentially less than or equal to 100° C., for example between 50 and 100° C.

The hydrogen pressure during step (b) is between about 0.1 and about 10 MPa and preferably between 1 and 5 MPa.

Performing step (b) under the conditions of the invention, especially the choice of the catalyst, makes it possible to limit the formation of byproducts: in particular, there is very little or even no formation of N,N,N',N'-tetramethyl-1,3-propanediamine, which would be difficult to separate from the diamine.

Step (c) concerns the removal of the fraction of alkali metal hydroxide introduced in step (b) that is soluble in the reaction medium (diamine+water) by evaporation of the diamine and of the water.

The fraction of alkali metal hydroxide that is soluble in the reaction medium may especially be removed by means of an evaporator. In the evaporator, the water and the majority of the diamine derived from step (b) pass into vapor phase and are directed toward a distillation column for step (d).

In one embodiment, the residual fraction of diamine associated with the alkali metal hydroxide leaving the evaporator may be recovered by decantation after dissolution of the alkali metal hydroxide in water.

According to this embodiment, the alkali metal hydroxide and the residual fraction of diamine leave at the bottom of the evaporator. Advantageously, a water supply makes it possible to dissolve the alkali metal hydroxide contained in this tail-stock of the evaporator. Finally, and advantageously, a decanter may be positioned at the bottom of the evaporator for recovering, on the one hand, the water-soluble alkali metal hydroxide, and, on the other hand, the diamine that is insoluble in the water+alkali metal hydroxide mixture, which may be redirected to the distillation column for step (d).

The distillation column of step (d) may be a side-withdrawal column or a wall column. Advantageously, the use of a side-withdrawal column or of a wall column makes it possible to improve the separation of the impurities contained in the diamine obtained, especially impurities such as N-methyl-1,3-diaminopropane and methylaminopropylamine.

The distillation may be performed at atmospheric pressure or under a gentle vacuum, for example at a pressure of between 80 and 95 kPa.

During the distillation, the water and the light byproducts leave at the top of the column. The removal of the diamine is performed on an intermediate removal between the top and bottom of the column, and the heavy byproducts leave at the bottom of the column.

The diamine obtained via the process of the invention is characterized by a purity of greater than 99.5%, especially greater than 99.8%.

The present invention also relates to a device for preparing a diamine, comprising:
 (a) at least a first reactor for the reaction between the corresponding monoamine and the corresponding alkenenitrile to form the corresponding aminonitrile, and a system for recycling the excess monoamine introduced;
 (b) a second reactor having means for separating out the catalyst for the hydrogenation of the aminonitrile obtained, in the presence of an alkali metal hydroxide, a hydrogenation catalyst and water;
 (c) an evaporator for separating out the alkali metal hydroxide that is soluble in the water+diamine mixture;
 (d) a distillation column for purifying the diamine.

The first reactor may be a piston reactor. It is possible to have several piston reactors in series.

The recycling system may consist of a separation system, especially a flash column and/or a distillation column and of a vacuum device associated with an absorption system.

The separation system makes it possible to recover:
 on the one hand, the aminonitrile, a first fraction of which is sent to the hydrogenation reactor and a second fraction of which is sent to an absorption system to enable dissolution of the excess monoamine; and on the other hand, the excess monoamine in gaseous form, which is sent, by means of a vacuum device, to the absorption system which enables its dissolution in the second fraction of aminonitrile, the whole then being sent to the first reactor.

Examples of vacuum devices that may be mentioned include a liquid ring pump, an ejector, a roots or dry pump, or an assembly of these devices. As examples of assemblies of vacuum devices, mention may be made, without being limited thereto, of the dry pump and then ejector assembly or the roots pump and then liquid ring pump assembly.

The absorption system may be an absorption column or a reactor.

The hydrogenation reactor may be a piston reactor or a stirred reactor.

The means for separating out the catalyst may be a decanter and/or a tangential filtration device.

In one embodiment, in the evaporator, the water and the majority of the diamine pass into vapor phase and are redirected to a distillation column for purification of the diamine.

In one embodiment, the residual fraction of diamine associated with the alkali metal hydroxide leaving the evaporator is recovered by decantation after dissolution of the alkali metal hydroxide in water.

According to this embodiment, the alkali metal hydroxide and the residual fraction of diamine leave at the bottom of the evaporator. Advantageously, a supply of water into the bottom of the evaporator makes it possible to dissolve the alkali metal hydroxide. Finally, and advantageously, a decanter may be positioned at the bottom of the column for recovering, on the one hand, the water-soluble alkali metal hydroxide, and, on the other hand, the diamine that is insoluble in the water+alkali metal hydroxide mixture, which may be directed to the distillation column for purification of the diamine.

The distillation column for purifying the diamine is advantageously a side-withdrawal column or a wall column.

All the essential and preferred characteristics of the process (P) apply to the device of the present invention.

The invention also relates to a continuous process (P1) for preparing an aminonitrile by reaction between the corresponding alkenenitrile and the corresponding monoamine, the monoamine being introduced in molar excess relative to the alkenenitrile with recycling of the unreacted monoamine into the reaction.

This process (P1) comprises all the essential and preferred characteristics of step (a) of the process (P).

Preferably, the aminonitrile is dimethylaminopropanenitrile, the monoamine is dimethylamine and the alkenenitrile is acrylonitrile.

Another subject of the invention is a continuous process (P2) for preparing diamine by reduction of an aminonitrile with hydrogen in the presence of at least one alkali metal hydroxide, water and a hydrogenation catalyst.

This process (P2) comprises all the essential and preferred characteristics of step (b) of the process (P).

Preferably, the diamine is dimethylaminopropylamine and the aminonitrile is dimethylaminopropanenitrile.

In addition, the process (P2) may comprise an additional step of separating out the alkali metal hydroxide by evaporation of the diamine obtained and of the water. This separation step corresponds to step (c) of process (P), and all these essential and preferred characteristics also apply to process (P2).

In addition, process (P2) may comprise a step of distillation of the diamine after the step of separating out the alkali metal hydroxide. This distillation step corresponds to step (d) of process (P), and all these essential and preferred characteristics also apply to process (P2).

The invention also relates to a process (P3) for separating a mixture of alkali metal hydroxide, water and diamine by evaporation of the diamine and of the water. This separation step corresponds to step (c) of process (P), and all its essential and preferred characteristics also apply to process (P3).

In addition, process (P3) may comprise a step of distillation of the diamine after the step of separating out the alkali metal hydroxide. This distillation step corresponds to step (d) of process (P), and all these essential and preferred characteristics also apply to process (P3).

The invention also relates to a process (P4) for distilling a diamine. This distillation step corresponds to step (d) of process (P), and all these essential and preferred characteristics also apply to process (P4).

The conversions obtained for each of the steps of the process of the invention and for process (P) in its entirety are greater than 99%.

The selectivity of each of the steps and of process (P) is, for its part, greater than 99%.

The examples that follow illustrate the process of the invention, in particular the advantages of this process.

EXAMPLE 1

Synthesis of DMAPN 680 kg/h of AN, 578 kg/h of DMA and 1397 kg/h of an 8.2% by weight solution of DMA in DMAPN are introduced via a static mixer into a tubular reactor maintained at 65° C. The reaction mixture leaving the reactor feeds a distillation column at 0.05 MPa.

The DMA leaving at the top of the column and also half the DMAPN leaving at the bottom are recycled into an absorption column functioning at 30° C. The production of DMAPN represents 1258 kg/h with a purity of greater than or equal to 99.6%.

EXAMPLE 2

Hydrogenation of the DMAPN 629 kg/h of DMAPN, 27 kg/h of water containing 0.1% NaOH and hydrogen to keep the pressure constant are introduced into a stirred reactor at 80° C. under a hydrogen pressure of 2.5 MPa. The reactor contains 5% by weight of Raney nickel doped with 1.6% by weight of Ti with 1.2 mol of NaOH per kg of nickel, and is equipped with a circulation loop comprising a tangential filter through which is withdrawn 681 kg/h of crude DMAPA.

EXAMPLE 3

Separation of the Alkali Metal Hydroxide and Distillation of the DMAPA 1362 kg/h of crude DMAPA feed an evaporator at atmospheric pressure. The compounds leaving at the top of the evaporator are sent in gaseous form into a distillation column. The compounds leaving at the bottom at 127° C. are withdrawn at a rate of 7.8 kg/h and are mixed with 0.25 kg/h of water, and a decanter enables separation, on the one hand, of the aqueous sodium hydroxide phase and, on the other hand, of the DMAPA, which is sent in liquid form to the distillation column. The distillation column functions at 0.095 MPa with a tail temperature of 145° C.

56 kg/h of water are recovered at the top of the column, containing about 3% of light amines;

1300 kg/h of an intermediate fraction of pure DMAPA with a titer of greater than or equal to 99.8% are withdrawn from the side of the column at a temperature of 133° C.;

6 kg/h constitute the column tailstock.

The invention claimed is:

1. A continuous process (P) for continuously preparing a diamine, the process comprising the steps of:
    (a) reacting a corresponding alkenenitrile and a corresponding monoamine to form a corresponding aminonitrile, the monoamine being introduced in molar excess relative to the alkenenitrile, with recycling into the reaction of the unreacted monoamine;
    (b) reducing the aminonitrile obtained in step (a) with hydrogen in the presence of at least one alkali metal hydroxide, water and a hydrogenation catalyst;
    (c) separating the at least one alkali metal hydroxide by evaporation of a diamine obtained in step (b) and of the water; and
    (d) distilling the diamine,
    wherein, said alkenenitrile is a linear or branched C2 to C4 alkene in which a hydrogen atom is replaced with a conjugated cyano group and/or the monoamine is a secondary amine of general formula R1R2NH, in which R1 and R2, which can be identical or different, represent a C1 to C4 alkyl.

2. The process as claimed in claim 1, wherein the monoamine is dimethylamine, the alkenenitrile is acrylonitrile, the aminonitrile is 3-(dimethylamino)propanenitrile and the diamine is dimethylaminopropylamine.

3. The process as claimed in claim 1, wherein step (a) is performed in one or more reactors in series of piston type with recycling of the excess monoamine and recycling of some of the aminonitrile.

4. The process as claimed in claim 1, wherein in step (a), the monoamine is introduced in an excess of at least 0.1 mol % relative to the alkenenitrile.

5. The process as claimed in claim 1, wherein the recycling of the monoamine uses a separation system, which makes it possible to recover:
    the aminonitrile, a first fraction of which is sent to a reactor for step (b) and a second fraction of which is sent to an absorption system to enable dissolution of the excess monoamine; and
    the excess monoamine in gaseous form, which is sent to said absorption system which enables its dissolution in said second fraction of aminonitrile.

6. The process as claimed in claim 1, wherein step (b) is performed in a reactor comprising means for separating out catalyst.

7. The process as claimed in claim 1, wherein the catalyst of step (b) is separated out, and all or part of this catalyst is regenerated before being recycled into the reaction (b).

8. The process as claimed in claim 1, wherein the catalyst of step (b) is a Raney metal.

9. The process as claimed in claim 1, wherein a fraction of alkali metal hydroxide that is soluble in the reaction medium is removed by means of an evaporator; and
    the water and the majority of the diamine derived from step (b) pass into vapor phase and are directed toward a distillation column for step (d).

10. The process as claimed in claim 9, for which a residual fraction of diamine associated with the alkali metal hydroxide leaving the evaporator is recovered by decantation after dissolution of the alkali metal hydroxide in water.

11. The process as claimed in claim 1, wherein in step (c), the distillation is performed using a side-withdrawal column or a wall column.

12. The process as claimed in claim 5, wherein the separation system is a flash column and/or a distillation column.

13. The process as claimed in claim 6, wherein the means for separating out the catalyst is a decanter and/or a tangential filtration system.

14. The process as claimed in claim 8, wherein the Raney metal is doped Raney nickel.

* * * * *